(12) United States Patent
Ohtake et al.

(10) Patent No.: US 9,336,598 B2
(45) Date of Patent: May 10, 2016

(54) SHAPE-EXTRACTION METHOD AND SHAPE-EXTRACTION SYSTEM

(75) Inventors: Yutaka Ohtake, Tokyo (JP); Hiromasa Suzuki, Tokyo (JP); Takuma Niizaka, Tokyo (JP); Daiki Yamanaka, Tokyo (JP)

(73) Assignee: The University of Tokyo, Tokyo (JP)

(*) Notice: Subject to any disclaimer, the term of this patent is extended or adjusted under 35 U.S.C. 154(b) by 90 days.

(21) Appl. No.: 14/131,198

(22) PCT Filed: Feb. 28, 2012

(86) PCT No.: PCT/JP2012/054889
§ 371 (c)(1),
(2), (4) Date: Feb. 19, 2014

(87) PCT Pub. No.: WO2013/005455
PCT Pub. Date: Jan. 10, 2013

(65) Prior Publication Data
US 2014/0169651 A1    Jun. 19, 2014

(30) Foreign Application Priority Data

Jul. 6, 2011   (JP) ................................. 2011-150024

(51) Int. Cl.
*G06K 9/00*     (2006.01)
*G06T 7/00*     (2006.01)
*G01N 23/04*    (2006.01)
*G06T 11/00*    (2006.01)

(52) U.S. Cl.
CPC ............ *G06T 7/0051* (2013.01); *G01N 23/046* (2013.01); *G06T 11/006* (2013.01); *G01N 2223/401* (2013.01); *G01N 2223/419* (2013.01); *G06T 2211/424* (2013.01); *G06T 2211/436* (2013.01)

(58) Field of Classification Search
None
See application file for complete search history.

(56) References Cited

U.S. PATENT DOCUMENTS 7,203,267 B2   4/2007  De Man

FOREIGN PATENT DOCUMENTS

| JP | 09-073558 A    | 3/1997 |
| JP | 11-025293 A    | 1/1999 |
| JP | 2002-024855 A  | 1/2002 |

(Continued)

OTHER PUBLICATIONS

Feldkamp, L. A., et al., "Practical Cone-Beam Algorithm," Journal of the Optical Society of America A 1(6):612-619, Jun. 1984.

(Continued)

*Primary Examiner* — Nirav G Patel
(74) *Attorney, Agent, or Firm* — Christensen O'Connor Johnson Kindness PLLC (57) ABSTRACT

An unknown surface shape of a physical object can be extracted with good precision. Image data of a projective image that has been acquired by radiation projection to an object is acquired. Next, a predetermined mesh structure is used to acquire cross-sectional images of the subject from image data of the projective images by reconstruction using tomography. Lattice points constituting the mesh structure are then moved in conformity with the surface shape of the object, based on the cross-sectional image that has been acquired by reconstruction. Reconstruction is carried out again using the mesh whose lattice point positions have been corrected. Movement on the reconstruction of the lattice points is then repeated as many times as required.

3 Claims, 12 Drawing Sheets

(56) References Cited

FOREIGN PATENT DOCUMENTS

| | | |
|---|---|---|
| JP | 2002-074386 A | 3/2002 |
| JP | 2003-123057 A | 4/2003 |
| JP | 2005-245830 A | 9/2005 |
| JP | 2007-102595 A | 4/2007 |
| WO | 2009/083864 A2 | 7/2009 |

OTHER PUBLICATIONS

Garland, M., and P. S. Heckbert, "Surface Simplification Using Quadric Error Metrics," Proceedings of the 24th Annual Conference on Computer Graphics and Interactive Techniques (SIGGRAPH '97), ACM Press/Addison-Wesley Publishing, N.Y., pp. 209-216.

Lorensen, W. E., and H. E. Cline, "Marching Cubes: A High Resolution 3D Surface Construction Algorithm," Computer Graphics 21(4):163-169, Jul. 1987.

Sitek, A., et al., "Tomographic Reconstruction Using an Adaptive Tetrahedral Mesh Defined by a Point Cloud," IEEE Transactions on Medical Imaging 25(9):1172-1179, Sep. 2006.

Yu, Y., et al., "Mesh Editing With Poisson-Based Gradient Field Manipulation," ACM Transactions on Graphics—Proceedings of ACM SIGGRAPH 23(3):644-651, Aug. 2004.

International Search Report mailed Apr. 24, 2012, in International Application No. PCT/JP2012/054889, filed Feb. 28, 2012, 2 pages.

Extended European Search Report mailed Feb. 2, 2015, issued in corresponding European Application No. EP 12 808 211.2, filed Feb. 28, 2012, 5 pages.

Soussen, C., and A. Mohammad-Djafari, "Polygonal and Polyhedral Contour Reconstruction in Computed Tomography," IEEE Transactions on Image Processing 13(11):1507-1523, Nov. 2004.

(a) outline of mesh deformation

FIG. 11A (b) optimum apex position and normal

SHAPE-EXTRACTION METHOD AND SHAPE-EXTRACTION SYSTEM

FIELD

The present disclosure relates to a method and a system for extracting a shape of an actual object, based on a radiation projection image of the actual object.

BACKGROUND

X-ray CT (Computed Tomography) is a technology with which it is possible to reconstruct an image of the inside of a subject (cross sectional image) based on X-ray intensity distribution (X-ray projection image) obtained by irradiating the subject (physical object) with X-rays from many directions. This type of CT has conventionally been widely used in healthcare applications, and recently has also been used in industry. By using X-ray CT, it is possible to identify a surface shape that cannot be seen from the outside, which makes it useful, for example, in the dimensional inspection and reverse engineering of products having complicated shapes.

In the reconstruction of cross-sectional images in X-ray CT, a regular lattice structure, for example, a mesh formed from a square lattice, is assumed. If a CT value of the outside of a component is made 0 and the CT value of the inside is made 1, in the case where a boundary line that delimits a surface shape (boundary line that separates the component and the outside) passes through a mesh, a CT value of that mesh will be greater than 0 and less than 1, and the surface shape will become blurred. In particular, there are many instances where if shapes of corner sections of a component are blurred, it makes identifying a shape difficult. With healthcare use, it is less problematic to have blurred components, but in industrial use, a solution to the problem of blurred images is necessary in order to identify the surface shape of a product.

On the other hand, the following foreign patent literature describes technology for acquiring images in conformity with the shape of a subject by causing lattice points to move in conformity with a specified shape: Japanese Patent Publication Nos. 2003-123057, 2002-24855, and 2002-74386. However, with each of these technologies, since it is a prerequisite that the shape of a subject has been obtained in advance in some way, it is difficult to apply to a subject of unknown shape. Also, the following foreign patent literature, describes technology for causing the lattice points to move based on a feature plane or feature edge line that has been designated by user: Japanese Patent No. 2007-102595. However, with this technology, even if it is possible to smooth the exterior appearance of an acquired subject shape, it is not always possible to match an acquired subject shape to an unknown subject shape. Also, the technology of Japanese Patent No. 2007-102595 is not for carrying out lattice deformation for matching to an unknown subject shape using values of an acquired cross-sectional image, which means it is not suitable for automatic or mechanical lattice point movement.

SUMMARY

Technical Problem

The present disclosure has been conceived in view of the above-described situation. An object of the present disclosure is to provide technology that can extract an unknown surface shape of a physical object with good precision.

Solution to Problem

Means for solving the above-described problem can be described as in the following aspects.

Aspect 1

A shape-extraction method comprising:

(1) a step of receiving image data of a projective image that has been acquired by radiation projection to an object;

(2) a step of using a predetermined mesh structure to acquire a cross-sectional image of the object from the image data of the projective image by tomographic reconstruction;

(3) a step of causing a lattice point that forms the mesh structure to move in conformity with the surface shape of the object based on the cross-sectional image that has been acquired by the reconstruction; and (4) a step of carrying out step (2) using a mesh that has had the position of the lattice point corrected using step (3), and then repeatedly executing step (3) and step (2) as many times as required.

Here, the radiation is a concept that includes x-rays, a neutron beam, and an electron beam.

Aspect 2

The shape-extraction method of aspect 1, wherein the processing for causing the lattice point to move in conformity with the surface shape of the object, in step (3), includes the following steps:

(3a) a step of approximating a boundary line between the object and portions outside of the object that passes through a convex polygon constituting the mesh structure and that shares a specified lattice point, to a straight line for each convex polygon; and (3b) a step of moving the specified lattice point to an intersection point of the straight line for each convex polygon, or to a point approximated to the intersection point.

Here, the convex polygon is a concept that includes a triangle. The convex polygon also includes a convex quadrilateral, pentagon, hexagon, etc.

Aspect 3

The shape extraction method of aspect 2, wherein the processing to approximate a boundary line between the object and a portion outside of the object to a straight line for each convex polygon, in step (3a), includes the following steps:

(3a1) a step of obtaining a normal to the boundary line, based on a gradient vector of image data of the convex polygon; and (3a2) a step of obtaining a position of the boundary line such that a ratio of divided surface areas of the convex polygon that has been divided by the boundary line corresponds to a value of image data of the convex polygon.

Aspect 4

The shape-extraction method of aspect 1, wherein the mesh structure is a tetrahedron mesh for producing a three-dimensional shape.

Aspect 5

The shape-extraction method of aspect 4, wherein the processing for causing the lattice point to move in conformity with the surface shape of the object, in step (3), includes the following steps:

(3p) a step of obtaining barycentric positions for two adjacent tetrahedron meshes that also include a boundary surface;

(3q) a step of obtaining a point constituting a predetermined CT value, between the barycentric positions of two tetrahedron meshes, as a barycenter of a triangle constituting a boundary mesh;

(3r) a step of obtaining orientation of the boundary mesh such that a normal direction of a triangle constituting the boundary mesh conforms to a gradient direction of the CT values of the two adjacent tetrahedron meshes; and (3s) a step of moving the lattice point using an apex position of the triangle constituting the boundary mesh that was obtained in steps 3q and 3r.

Aspect 6

A shape-extraction system, provided with a projective image-receiving section, a cross section reconstruction section, a lattice point movement section, and a surface shape output section, wherein:

the projective image-receiving section receives image data of a projective image that has been acquired by radiation projection to an object, the cross section reconstruction section uses a predetermined mesh structure to acquire a cross-sectional image of the object from the image data of the projective image by reconstruction using tomography, the lattice point movement section is configured to carry out:

(1) processing to cause a lattice point that forms the mesh to move in conformity with the surface shape of the object, based on the cross-sectional image that has been acquired by the reconstruction, and (2) processing to send a mesh that has had the lattice point position corrected by the processing of (1) above to the cross section reconstruction section, and acquiring an updated cross-sectional image from the cross section reconstruction section, and the surface shape output section outputs the updated cross-sectional image.

Aspect 7

The shape-extraction system of aspect 6, wherein the mesh structure is a tetrahedron mesh for producing a three-dimensional shape.

Aspect 8

A computer program for executing the shape-extraction method of any one of aspect 1 to aspect 5 using a computer.

Advantageous Effects

According to the present disclosure, it is possible to provide technology that can extract an unknown surface shape of a physical object with good precision. Also, according to the present disclosure, since movement of lattice points is carried out based on cross-sectional images that have been acquired by reconstruction, it is easy to automate movement of lattice points.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A shape-extraction system and a shape extraction device of a first embodiment of the present disclosure will be described in the following with reference to FIGS. 1-9.

Structure of the First Embodiment

Figure 1:
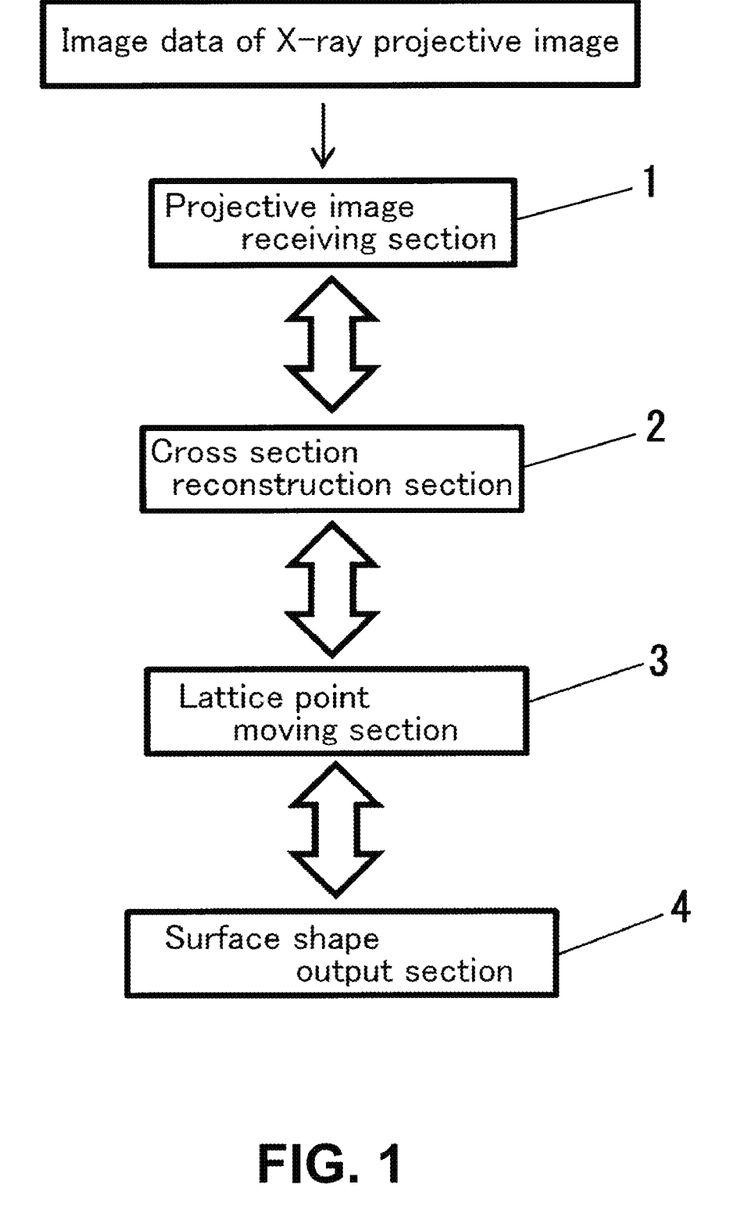
FIG. 1 is a block diagram showing the schematic structure of a shape extraction system of a first embodiment of the present disclosure.

A shape-extraction system of this embodiment is provided with a projective image-receiving section 1, a cross section reconstruction section 2, a lattice point movement section 3, and a surface shape output section 4. Each of these functional elements can basically be configured using computer programs.

The projective image-receiving section 1 receives image data of a projective image that has been acquired by radiation projection to an object. Here, the radiation is not only x-rays, but also includes a neutron beam and an electron beam. Also, the projection image is not only a transmission image, but also includes a reflected image.

The cross section reconstruction section 2 uses a predetermined mesh structure to acquire cross-sectional images of the subject from image data of the projective image by reconstruction using tomography (known as CT).

The lattice point movement section 3 is configured to carry out the following: (1) processing to move lattice points constituting the mesh in conformity with the surface shape of the object, based on cross-sectional images that have been acquired by reconstruction, and (2) processing to send a mesh that has had the lattice point position corrected by the processing of (1) above to the cross section reconstruction section 2, and acquiring an updated cross sectional image from the cross section reconstruction section 2.

Detailed operation of the lattice point movement section 3 will be described later.

The surface shape output section 4 outputs the updated cross-sectional image to a suitable memory or to a subsequent process.

Shape Extraction Method of the First Embodiment

Next, a shape-extraction method that uses the previously described system will be described in detail with reference to the flowchart of FIG. 2. In the following, description will be given using x-rays exemplifying the radiation.

Figure 2:
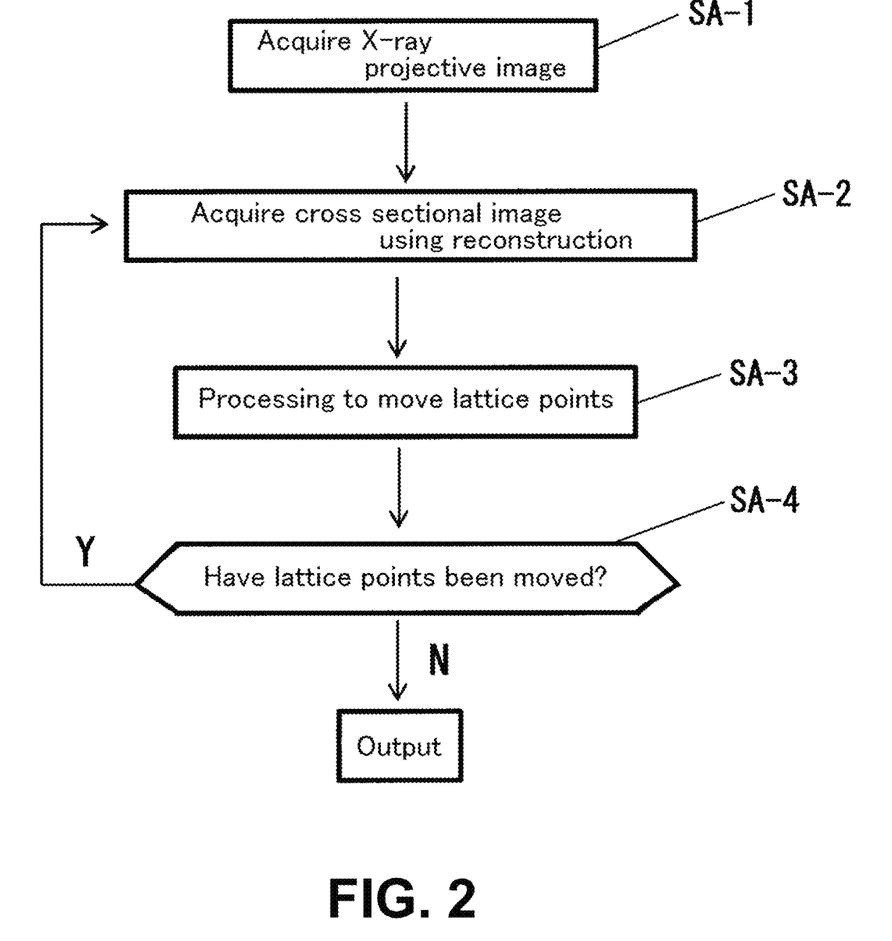
FIG. 2 is a flowchart showing the schematic procedure of a shape-extraction method of the first embodiment of the present disclosure.

Step SA-1 in FIG. 2

Figure 3A:
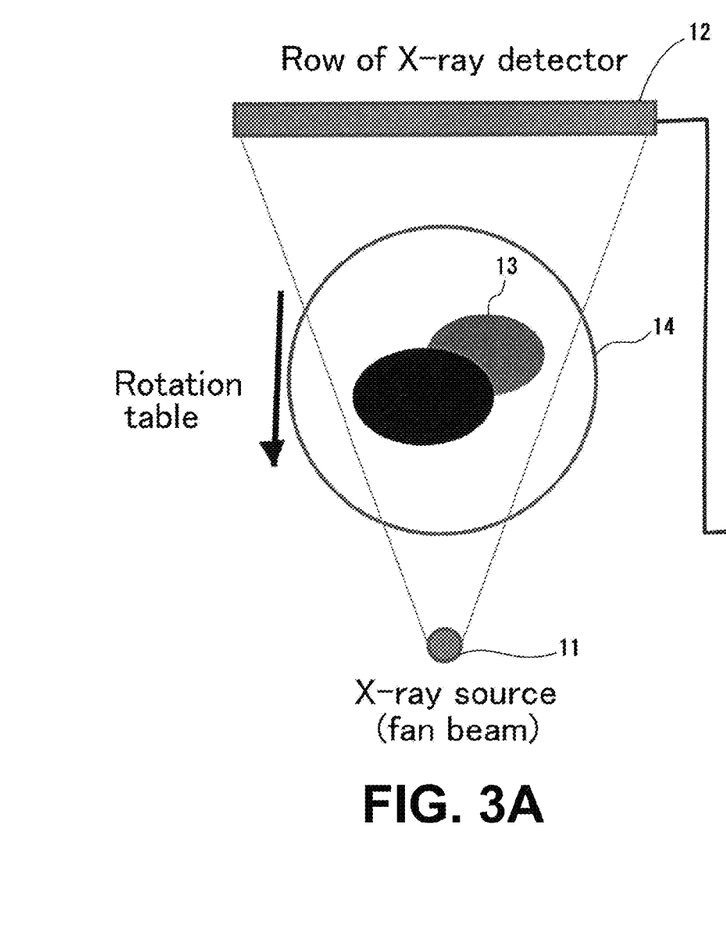
FIGS. 3A and 3B are explanatory drawings for describing a projection image acquisition method of the first embodiment of the present disclosure.
Figure 3B:
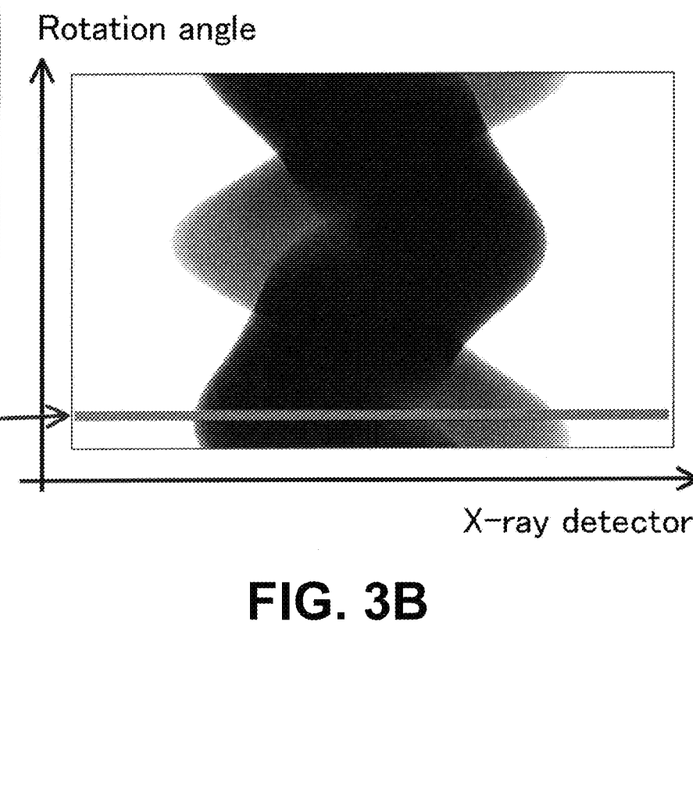

First, an x-ray projection image (with this embodiment, an x-ray transmission image) is obtained by a projection of irradiation to an object. A method of acquiring the x-ray projection image will be described with reference to FIG. 3. With this example, an object 13 is placed between an x-ray source 11 and an x-ray detector 12. This object 13 is mounted on a rotation table 14. If x-rays are projected to the object 13 while the object 13 is rotated by the rotation table 14, it is possible to acquire an x-ray projection image such as is shown in FIG. 3B from the x-ray detector 12. With the illustrated example, a so-called fan beam structure is shown where acquisition of one-dimensional projective images is repeated, but it is also possible to adopt a cone beam structure with which it is possible to acquire two-dimensional projective images simply by rotating the subject. As a method of acquiring x-ray projection images, it is possible to use a similar method to that in the related art, and so further detailed description will be omitted.

With the system of this embodiment, image data for a projection image that has been created as described above is received by the projective image-receiving section 1.

Step SA-2 in FIG. 2

Figure 4A:
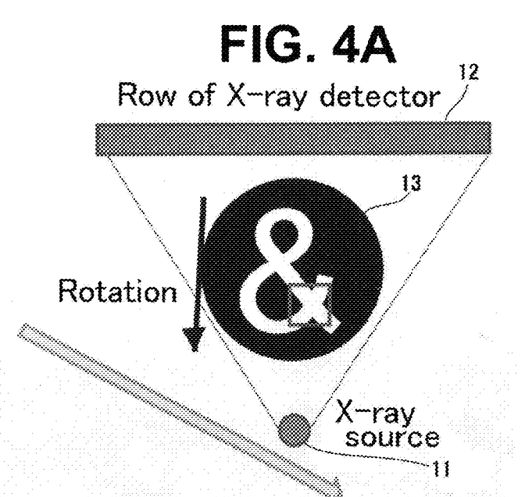
FIGS. 4A-4F are explanatory drawings for explaining the shape-extraction method of the first embodiment of the present disclosure.
Figure 4B:
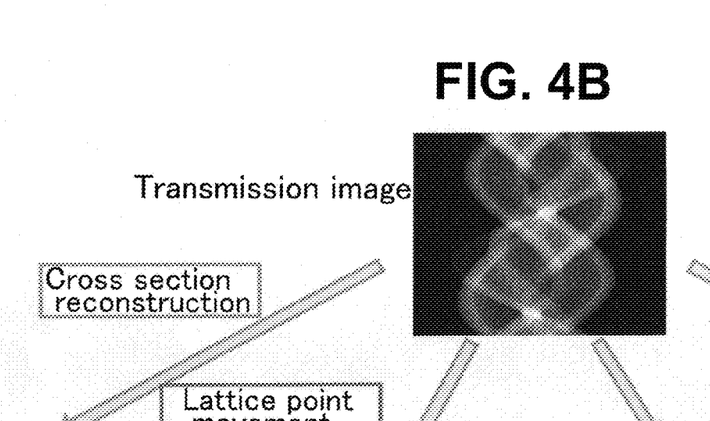
Figure 4C:
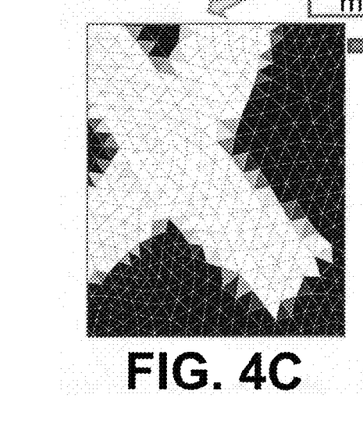

Next, a predetermined mesh structure is used to acquire cross-sectional images of the subject from image data of the projective images by reconstruction using tomography. This step will be further described with reference to FIG. 4. With the example of FIG. 4, the object shown in FIG. 4A is used. The obtained projection image (transmission image with the above example) is shown in FIG. 4B. Further, with this example, the triangular mesh structure shown in FIG. 4C is used as the predetermined mesh structure. On the premise of this mesh structure, it is possible to reconstruct a cross section image of the object using tomography. As a method for reconstructing cross-sectional images using tomography, it is possible to use a conventional method such as ML-EM (Maximum Likelihood—Expectation Maximization), and so detailed description will be omitted. Also, a cross-sectional image acquired through reconstruction is shown in FIG. 4C. Here, portions shown in half tone (gray) are recognized as "blur."

Step SA-3 in FIG. 2

Next, lattice points constituting the mesh structure are moved in conformity with the surface shape of the object, based on the cross-sectional image that has been acquired by reconstruction. A procedure for moving the lattice points will be described in detail with reference to FIG. 5.

Figure 5:
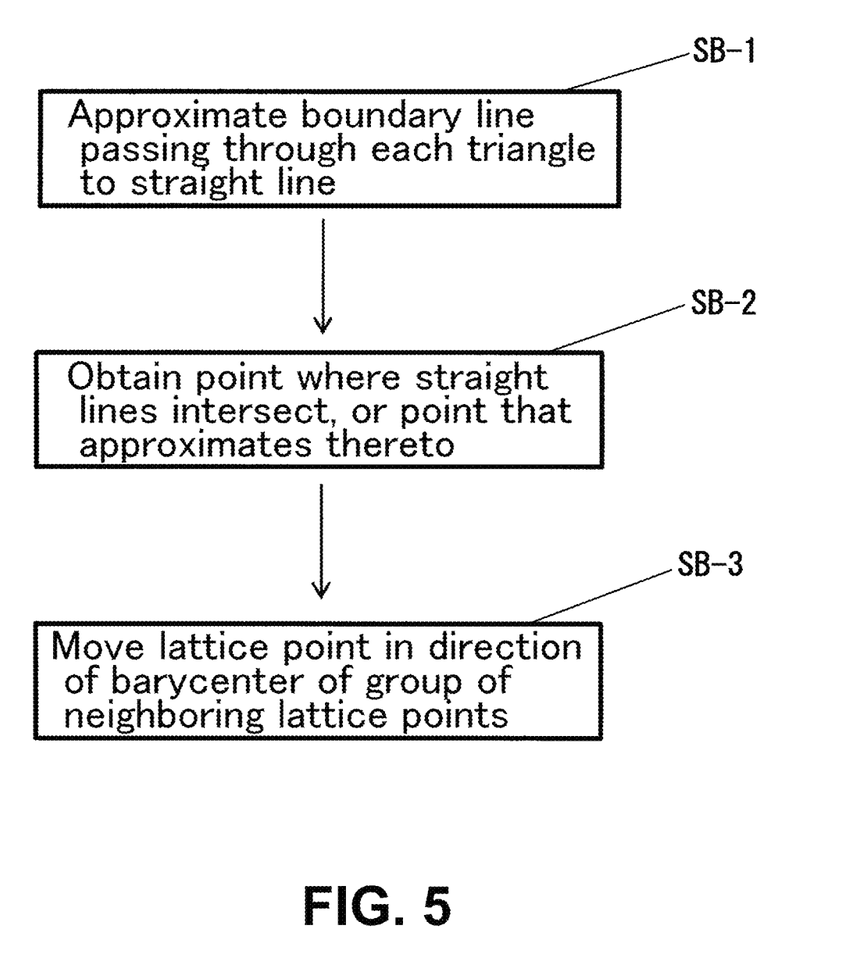
FIG. 5 is a flowchart for describing a procedure for moving lattice points in the first embodiment of the present disclosure.

Step SB-1 in FIG. 5

First, a boundary line passing through each triangle constituting the mesh structure is approximated to a straight line. As will be understood, the position of the actual boundary line is unclear in this step, and so some sort of estimation is necessary. With this embodiment therefore, as described in the following, a method is used whereby first a normal of the boundary line is calculated, and secondly a position of a straight line is calculated. It is possible to reverse the order of these calculations.

Calculation of the Boundary Line Normal

A normal of the estimated boundary line can be calculated using a gradient vector of the CT value.

First, it is assumed that a straight line approximation of a boundary of triangle T is a set of points x that satisfy the following equation:

$$n_T \cdot (x - p_T) = 0$$

[$n_T$: unit normal vector, $p_T$: point where straight line passes through]

Then, the entire mesh is subjected to translation by a microscopic amount in a positive direction of each axis (with this example, the x-axis and the y-axis), and CT reconstruction is carried out. Here, the amount of movement in the x-axis direction is made δx, and the amount of movement in the y-axis direction is made δy.

Figure 6:
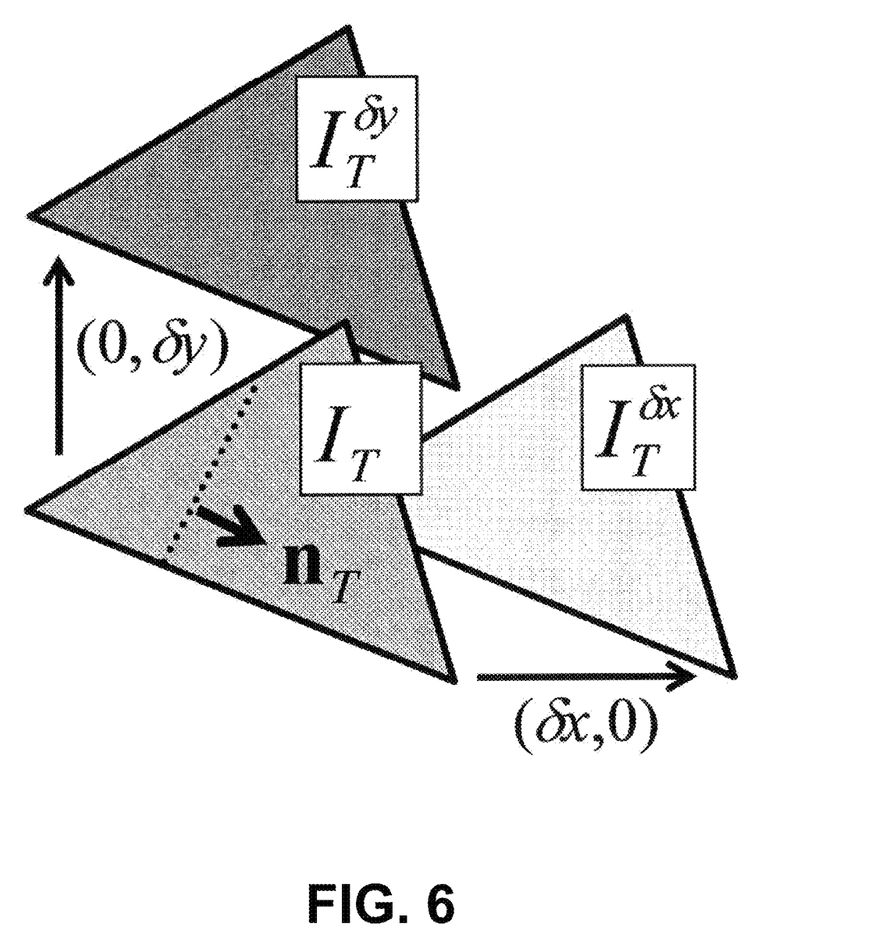
FIG. 6 is an explanatory drawing for describing a procedure for moving lattice points in the first embodiment of the present disclosure.

Next, a unit normal vector $n_T$ for the triangle T is calculated from the following equation (refer to FIG. 6):

$$n_T = (I_T^{\delta x} - I_T, I_T^{\delta y} - I_T) / \sqrt{(I_T^{\delta x} - I_T)^2 + (I_T^{\delta x} - I_T)^2}$$

$I_T$: CT value with no translation
$I_T^{\delta x}$: CT value of mesh that has been moved in the x axis direction
$I_T^{\delta y}$: CT value of mesh that has been moved in the y axis direction In this way it is possible to obtain a normal to the estimated boundary line. Specifically, it is possible to determine orientation of the boundary line using this normal.

Estimation of Boundary Line Position

The position of the boundary line can be estimated as follows:

First, as described above, a straight line approximation of a boundary surface of triangle T is a set of points x that satisfy the following equation.

$$n_T \cdot (x - p_T) = 0$$

[$n_T$: unit normal vector, $p_T$ point passing through straight line]

Figure 7:
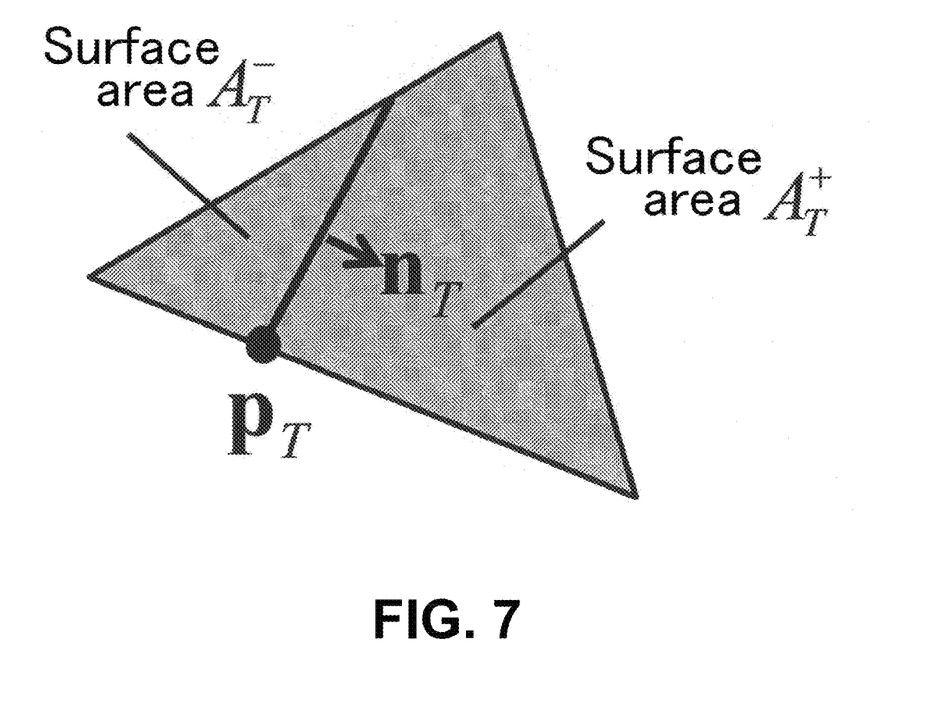
FIG. 7 is an explanatory drawing for describing a procedure for moving lattice points in the first embodiment of the present disclosure.
Figure 8:
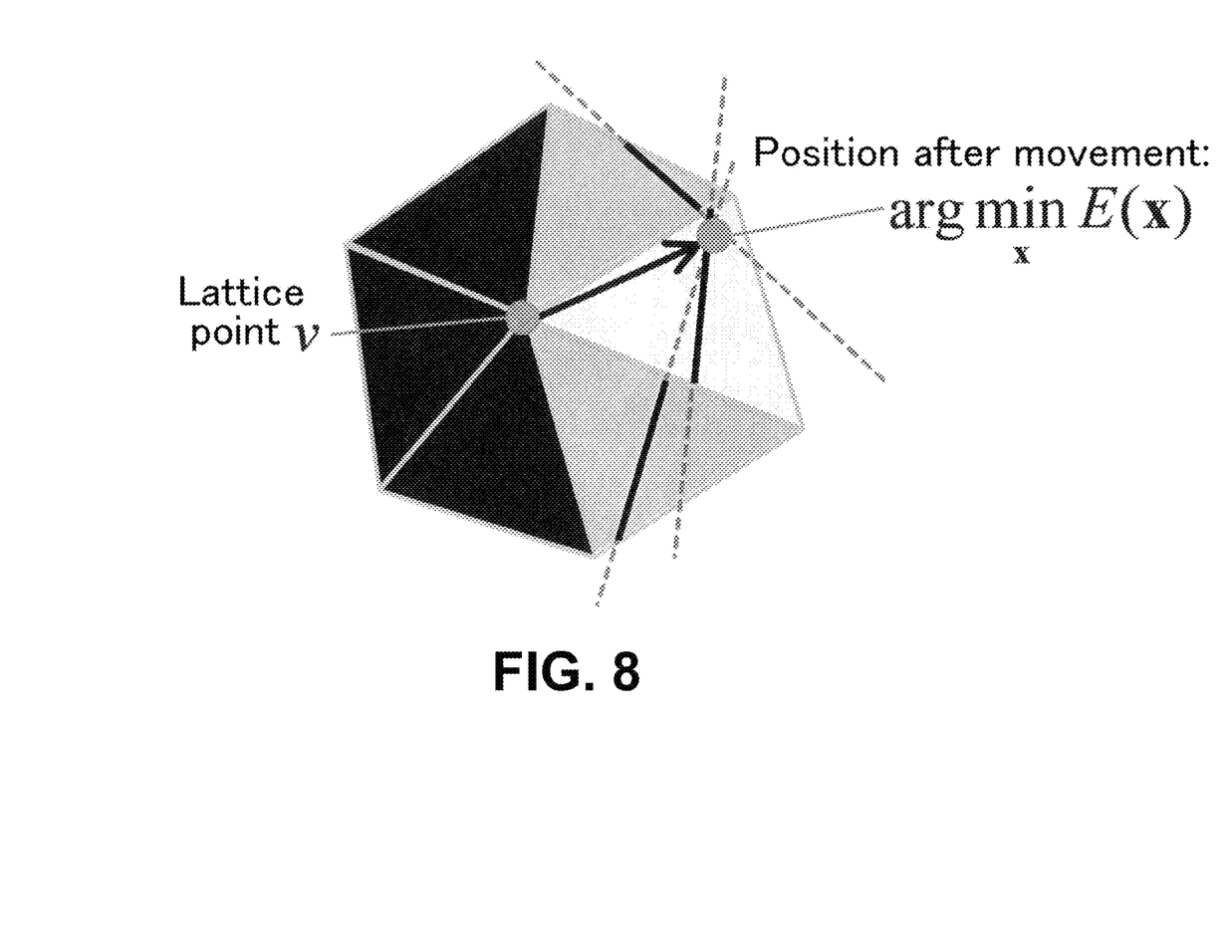
FIG. 8 is an explanatory drawing for describing a procedure for moving lattice points in the first embodiment of the present disclosure.

Then, point $p_T$ is placed on an edge, of the three edges of triangle T, where an orthogonal projection to a straight line having a direction of vector $n_T$ becomes longest, and a ratio of surface areas of the triangle that has been divided by the straight line (specifically, an internal ratio) satisfies the following equation (refer to FIG. 7):

$$A_T^+ : A_T^- = W - I_T : I_T - B$$

$A_T^+$: for T divided by a straight line, surface area of forward positive side of $n_T$
$A_T^-$: for T divided by a straight line, surface area of negative direction side of $n_T$
$I_T$: CT value of triangle
W: CT value (constant) of object
B: CT value (constant) of air Using this condition, it is possible to estimate the position of a boundary line between the object and the air. If the position and orientation of the boundary line are known, it is possible to acquire a straight line that passes through the triangular region (namely, the boundary line).

Step SB-2 in FIG. 5

Next, intersection points of the straight lines that have been acquired for each region, or points that approximate thereto, are obtained. Specifically, it is possible to carry out calculations as follows.

Lattice point v is moved to a point x where E(x) below is minimum. Here, since the three or more straight lines generally do not cross at a single point; with this embodiment, a point where a square sum of distance to the straight lines is the minimum is substituted for the single point (refer to the following equation):

$$E(x) = \sum_{T \in N(v)} (n_T \cdot (x - p_T))^2$$

N(v): set of triangles having lattice point v as apex and CT value that is blurred In this way, it is possible to place a single lattice point on the estimated boundary line. By applying this operation to the triangular meshes that are blurred, it is possible to move each lattice point. If the moved lattice points are connected, it is possible to acquire the estimated boundary line.

Step SB-3 in FIG. 5

Next, lattice points that have been moved with the previously described procedure are further moved on the boundary line. Specifically, a barycentric position for lattice points surrounding the lattice point is first calculated. Then, the lattice point is moved to a position that is closest to the barycentric point on the boundary line. In this way, there is the advantage that it is easy to carry out reconstruction using an ML-EL method.

Step SA-4 in FIG. 2

Figure 4D:
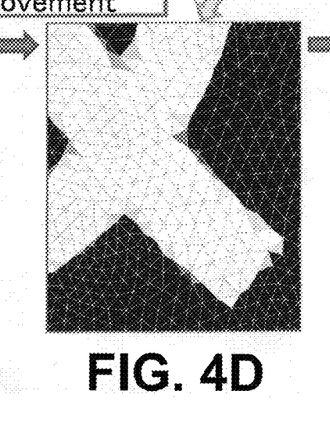
Figure 4E:
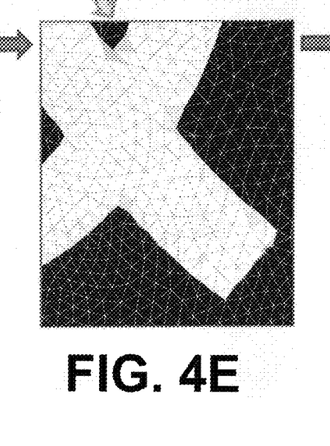
Figure 4F:
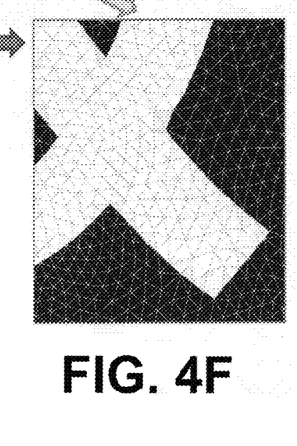

Next, it is determined whether or not the lattice point has actually moved in steps up to the aforementioned. In the case where the lattice point has moved, a moved lattice point is assumed and processing of the previous step, SA-2 to SA-4, is repeated. The result of carrying out lattice movement and repeating the reconstruction is shown in FIGS. 4D-4F In the case where the lattice point has not moved, a finally obtained cross-sectional image is output. The output destination can be set in accordance with the intended use of the data, but is, for example, a memory for data storage or a process for additional processing.

With conventional CT reconstruction, calculation was performed using a square and regular lattice. Differing from this, with the procedure of the embodiment described above, the shape of the lattice is a convex polygon, and calculation for reconstruction is carried out using an irregular (unstructured) lattice (although it is also possible to use a regular lattice in an initial state). Further, with this embodiment, the shape of this lattice can be changed dynamically. These points constitute the feature of the above-described procedure.

Example

Next, with reference to FIG. 9, a specific example using the above-described embodiment will be described by comparison with a conventional method.

Figures 9A, 9B:
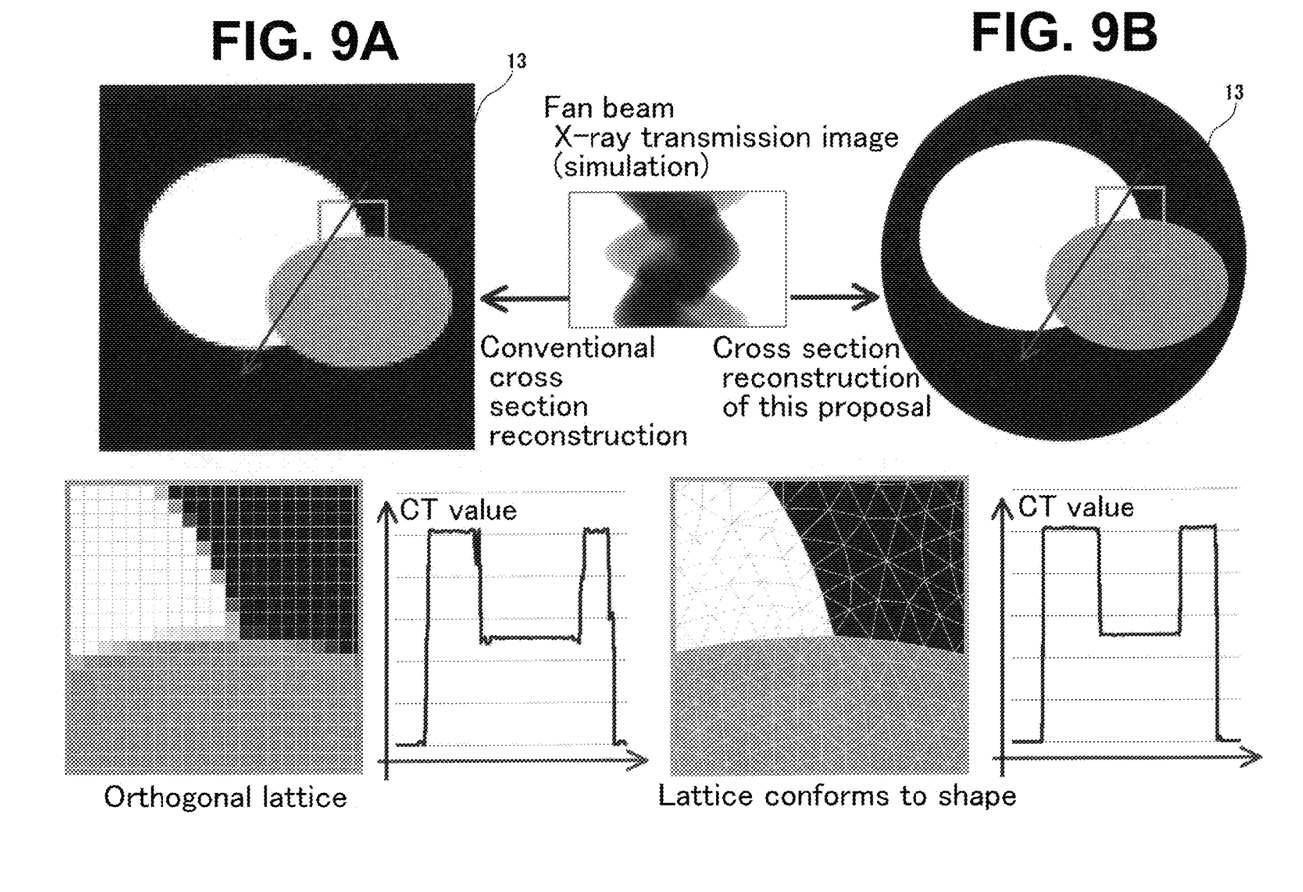
FIGS. 9A and 9B are explanatory drawings for describing the advantages of the shape-extraction method of the first embodiment of the present disclosure, with FIG. 9A showing extraction results using the conventional method, and FIG. 9B showing extraction results using the method of the embodiment.

With the conventional method FIG. 9A), blurring is noticeable on the boundary line, as will also be understood from CT values of a cross-section in the direction of the arrows in the drawing. Conversely, with the example FIG. 9B), the boundary line is clear and there is little blurring. This effect is particularly striking at corner sections of the object. With the example of FIG. 9, CT values of the object (subject) can be regarded as having three types. In this type of case, in the case where preliminary CT values can be anticipated, it is also possible to predict the boundary line by applying the previously described method to each boundary between two materials.

According to the method of this embodiment, therefore, there is the advantage that it is possible in an industrial situation, for example, to accurately acquire the shape of a component, being the object, in an industrial application.

Second Embodiment of the Present Invention

Next, a shape-extraction method and shape extraction device of a second embodiment of the present disclosure will be described with reference to FIG. 10. In the description of this embodiment, elements that are basically common to the above-described first embodiment are assigned the same reference numerals, and cumbersome description will be avoided.

With the above-described first embodiment, it was possible to extract the surface shape of a subject by using a triangular mesh as a mesh structure. Differing from this, the second embodiment described in the following extracts a solid shape by using a tetrahedron mesh as the mesh structure. Also, with the first embodiment an ML-EL method was adopted as the CT reconstruction method. Differing from this, with the second embodiment an already-known Feldkamp method (Feldkamp, L. A., et al., "Practical Conebeam Algorithm," J. Opt. Soc. Am. a, 1:612-619, 1984.) is used. In this way it is possible, with the second embodiment, to obtain CT values f(c) at a barycenter c of each tetrahedron constituting the mesh. Here, a CT value f(c) at the barycenter of each tetrahedron can be treated as a CT value representing the element (the mesh).

However, even in the case of extracting a solid shape, the device and method for extracting a solid shape are basically common to the above-described first embodiment. Specifically, each of the steps shown in FIG. 2 are common to both embodiments, and the block diagram shown in FIG. 1 is also common. It is essentially necessary, however, to make the following word replacements:

2D⇒3D
polygon⇒polyhedron
Triangle⇒tetrahedron
Straight line⇒planar surface
boundary line⇒boundary surface
surface area⇒volume It is therefore necessary to slightly change the steps shown in SB-1 to SB-3 in FIG. 5. In the following, description of steps SC-1 to SC-3 corresponding to each step in FIG. 5 is based on FIG. 10. Each step of FIG. 10 also, similar to the case in FIG. 5, shows an example for shaping the step SA-3 of FIG. 2.

Figure 10:
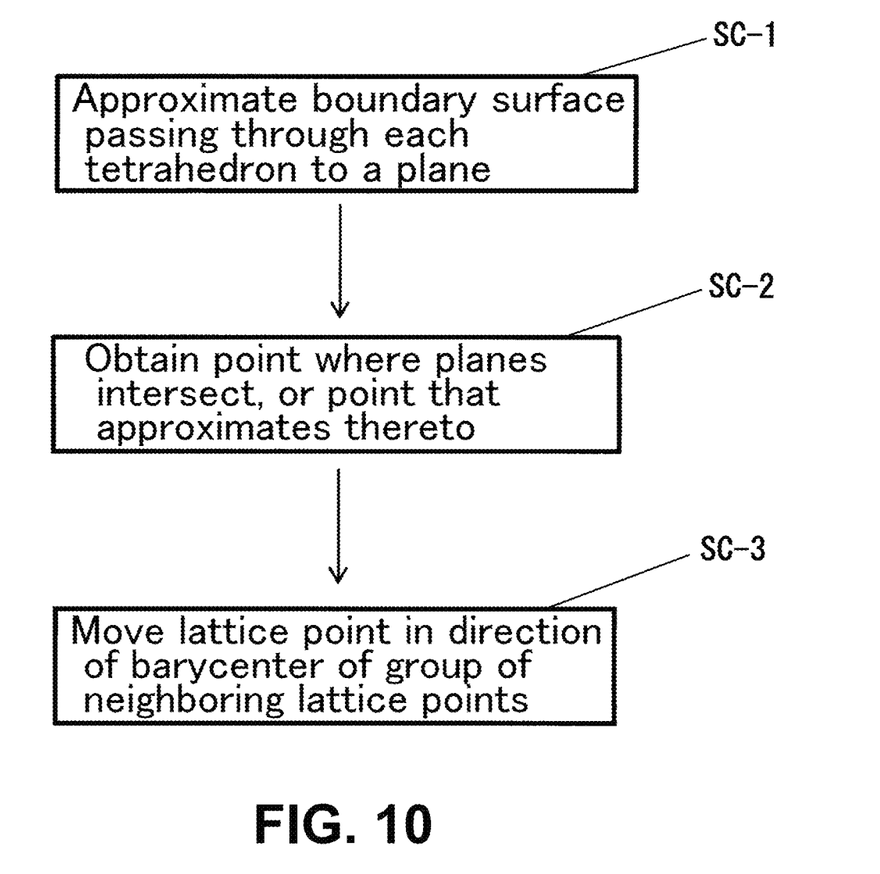
FIG. 10 is a flowchart for describing a procedure for moving lattice points in a second embodiment of the present disclosure.

Step SC-1 in FIG. 10

First, processing to approximate a boundary surface passing through each tetrahedron constituting the mesh structure to a planar surface will be described.

Detection of Material Boundary Using Binarization

First, detection of a material boundary is carried out using CT values inherent to the material (already known). In the case where CT values for two types of material A and B are already known, a CT value Ft at a boundary surface between material A and material B is obtained as an average value of the CT values for A and B. With this example, since a component of a single material that has been placed in the atmosphere is assumed, material A is air and material B is the component. By comparing this value and the CT value of each tetrahedron, it is possible to differentiate a tetrahedron included in material A and a tetrahedron included in material B. It is then possible to obtain a boundary mesh M as a set of triangles (triangles constituting surfaces of the tetrahedrons), commonly contained in tetrahedrons of material A and tetrahedrons of material B. Accordingly, an individual boundary mesh is a planar surface mesh of triangles. In this state, the boundary line surface usually passes through the inner part of a tetrahedron mesh positioned on the boundary, but as will be understood, at what position of the mesh it passes is not known. Accordingly, at this point in time, a boundary mesh M does not usually conform to the boundary surface of the subject body.

Calculation of Planar Surface Representing Boundary Surface

Processing to approximate a position of the boundary mesh M to an ideal boundary surface by moving the position of the obtained boundary mesh M will be described in the following. As a prerequisite, the optimum position of the boundary mesh M is considered to be as follows. Specifically, in order to be the optimum (namely, corresponding to a boundary surface) boundary mesh M, the following are necessary:

a barycenter m, of a triangle constituting the boundary mesh must be on the material boundary; and a normal of that triangle must be equivalent to a gradient direction of a CT value of that barycentric point (namely, a direction in which CT value increases or decreases).

Figure 11A:
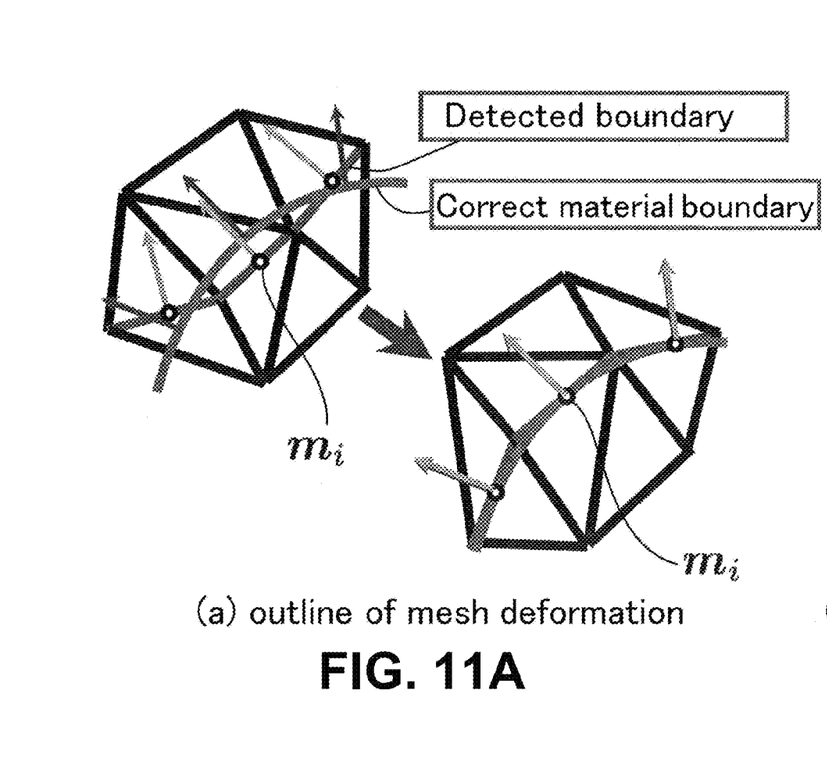
FIGS. 11A and 11B are explanatory drawings for describing boundary mesh deformation processing.

How the barycentric position and normal direction of the detected boundary surface change at the correct material boundary is schematically shown in FIG. 11A. However, "correct material boundary" here is not known at this point in time. In the description here, therefore, the description is for "conditions that are supposed to be satisfied if an obtained boundary is correct." From now on, a barycentric position after movement will be represented by $m'_i$.

Calculation of Optimal Material Boundary

Figure 11B:
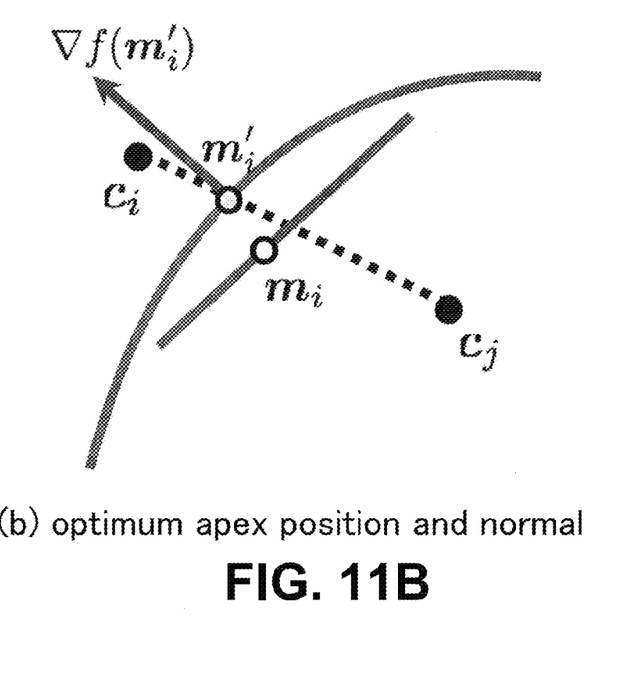
Figure 12:
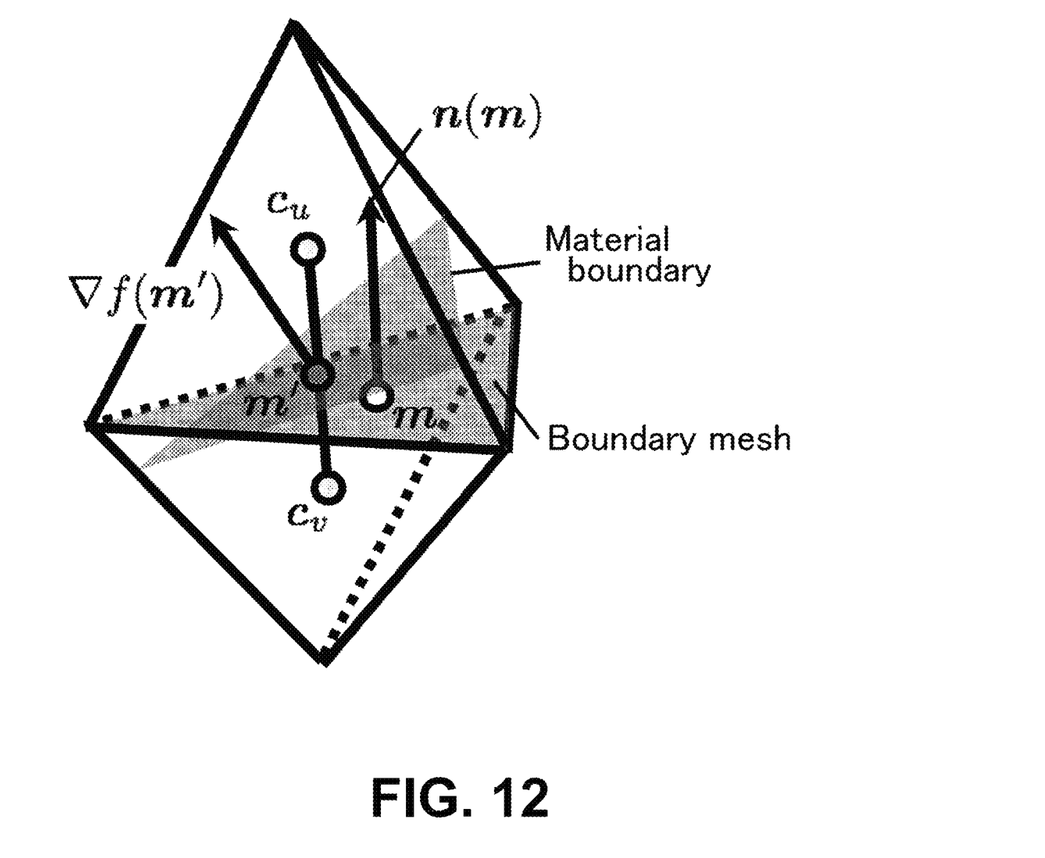
FIG. 12 is an explanatory drawing for describing boundary mesh deformation processing.

A position $m'_i$ of a barycenter of a triangle constituting an optimum boundary mesh M is a point between barycenters $c_i$ and $c_j$ of two tetrahedrons including the boundary, where $f(m'_i)=F_t$ (refer to FIG. 11B and FIG. 12).

$F_t$ is generally a number that a user can easily designate. For example, in the case where two things that touch at the boundary are air and an object, then since respective CT values are themselves generally known, it is possible to make $F_t$ between those two values.

Also, a normal to a triangle constituting the optimum boundary mesh is a vector $n(m'_i)$ for which a gradient $\nabla f(m'_i)$ of a CT value for an obtained position $m'_i$ has been normalized. $\nabla f(m'_i)$ can be obtained using central difference, as in the following equation:

$$\nabla f(m') = \left( \frac{f(m'+dx) - f(m'-dx)}{2|dx|}, \right.$$
$$\left. \frac{f(m'+dy) - f(m'-dy)}{2|dy|}, \frac{f(m'+dz) - f(m'-dz)}{2|dz|} \right)$$

As a result of the above described processing, it is possible to acquire a boundary mesh M positioned on the material boundary surface. Specifically, it becomes possible to approximate the boundary surface to a planar surface.

Step SC-2 in FIG. 10

Movement of Apex

Apexes of adjacent meshes M are expected to align at both ends of edges constituting the boundary. However, with a boundary mesh that has been acquired as described above, the apexes do not generally align.

QEM (quadric error metrics) is therefore used in order to cause the apexes of the boundary mesh M to move to an optimum position. Specifically, a position at which E(p), being a square of distance between each apex point p of the boundary mesh M and a planar surface of a boundary mesh that has been estimated as described above becomes minimum, is obtained. E(p) is represented by the following formula:

$$E(p) = \sum_{t_i \in N(p)} \{(n(m'_i) \cdot (p - m'_i))\}^2$$

N(p) here represents a group of triangles that are adjacent to the apex p, while $m'_i$ and $n(m'_i)$ represent optimum barycentric position and normal of respective triangles $t_i$.

Re-Mesh

In the case of moving an apex using QEM, there may be cases in which a drawback arises where the mesh is reversed. In this type of case, it is preferable to carry out generating a new mesh (known as re-mesh). An already known re-mesh method can be used, and so detailed description will be omitted.

Step SC-3 in FIG. 10

Next, using E(p) obtained as described above, an extension point is moved such that that value becomes minimum. This step corresponds to step SB-3 in FIG. 5.

Subsequent processing is the same as that after SA-4 in FIG. 2 in the description of the first embodiment, and so detailed description will be omitted. Also, the structure of the device and method of the second embodiment other than described above can be the same as for the first embodiment.

The present disclosure is not limited to the above-described embodiments, and various modifications can additionally be obtained within a scope that does not depart from the spirit of the disclosure.

For example, each of the above-described structural elements can exist as a functional block, and can also exist as independent hardware. Also, as a method of implementation, it is possible to use hardware or to use computer software. Further, a single functional element of the present disclosure may be realized as a set of a plurality of functional elements, and a plurality of functional elements of the present disclosure may be implemented by a single functional element.

It is also possible for each functional element constituting the present disclosure to exist separately. In the case of existing separately, necessary data can be exchanged by means of a network, for example. Similarly, it is also possible for each function of an internal part of each section to exist separately. For example, it is possible to implement each functional element, or some of the functional elements, of this embodiment using grid computing or cloud computing.

Also, in the above-described first embodiment, a mesh is constructed using triangles, but it is also possible to use different convex polygons instead of triangles.

The invention claimed is:

1. A shape-extraction method comprising:
   (1) a step of receiving image data of a projective image that has been acquired by radiation projection to an object;
   (2) a step of using a predetermined mesh structure to acquire a cross-sectional image of the object from the image data of the projective image by reconstruction using tomography;
   (3) a step of causing a lattice point that forms the mesh structure to move in conformity with the surface shape of the object based on the cross-sectional image that has been acquired by the reconstruction; and
   (4) a step of carrying out step (2) using a mesh that has had the position of the lattice point corrected using step (3), and then repeatedly executing step (3) and step (2) as many times as required;
   wherein the mesh structure is a tetrahedral mesh for producing a three-dimensional shape, and
   wherein the processing for causing the lattice point to move in conformity with the surface shape of the object, in step (3), comprises:
   (3p) a step of obtaining barycentric positions for two adjacent tetrahedron meshes that also include a boundary surface;

(3q) a step of obtaining a point constituting a predetermined CT value, between the barycentric positions of two tetrahedron meshes, as a barycenter of a triangle constituting a boundary mesh;

(3r) a step of obtaining orientation of the boundary mesh such that a normal direction of a triangle constituting the boundary mesh conforms to a gradient direction of the CT values of the two adjacent tetrahedron meshes; and (3s) a step of moving the lattice point using an apex position of the triangle constituting the boundary mesh that was obtained in steps 3q and 3r.

2. A non-transitory computer-readable medium having program instructions stored thereon, wherein, in response to execution by one or more computing devices, the program instructions cause the one or more computing devices to execute a shape-extraction method comprising:

(1) a step of receiving image data of a projective image that has been acquired by radiation projection to an object;

(2) a step of using a predetermined mesh structure to acquire a cross-sectional image of the object from the image data of the projective image by reconstruction using tomography;

(3) a step of causing a lattice point that forms the mesh structure to move in conformity with the surface shape of the object based on the cross-sectional image that has been acquired by the reconstruction; and (4) a step of carrying out step (2) using a mesh that has had the position of the lattice point corrected using step (3), and then repeatedly executing step (3) and step (2) as many times as required;

wherein the processing for causing the lattice point to move in conformity with the surface shape of the object, in step (3), comprises:

(3a) a step of approximating a boundary line between the object and portions outside of the object, the boundary line passing through a convex polygon that constitutes the mesh structure and that shares a specified lattice point, to a straight line for each convex polygon; and (3b) a step of moving the specified lattice point to an intersection point of the straight line for each convex polygon, or to a point approximated to that intersection point.

3. The computer-readable medium of claim 2, wherein the processing to approximate a boundary line between the object and portions outside of the object to a straight line for each convex polygon, in step (3a), comprises:

(3a1) a step of obtaining a normal to the boundary line, based on a gradient vector of image data of the convex polygon; and (3a2) a step of obtaining a position of the boundary line such that a ratio of divided surface areas of the convex polygon that has been divided by the boundary line corresponds to a value of image data of the convex polygon.

* * * * *